United States Patent
Mohl

(10) Patent No.: US 12,270,401 B2
(45) Date of Patent: *Apr. 8, 2025

(54) DEVICE TO ASSIST THE PERFORMANCE OF A HEART

(71) Applicant: Miracor Medical SA, Awans (BE)

(72) Inventor: Werner Mohl, Altenmarkt-Thenneberg (AT)

(73) Assignee: Miracor Medical SA (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/906,911

(22) Filed: Oct. 4, 2024

(65) Prior Publication Data

US 2025/0027498 A1   Jan. 23, 2025

Related U.S. Application Data

(60) Continuation of application No. 18/795,656, filed on Aug. 6, 2024, which is a continuation of application
(Continued)

(30) Foreign Application Priority Data

Feb. 27, 2007   (AT) .................. A 306/2007

(51) Int. Cl.
*A61M 60/523*      (2021.01)
*A61M 60/13*       (2021.01)
(Continued)

(52) U.S. Cl.
CPC .......... *F04D 13/027* (2013.01); *A61M 60/13* (2021.01); *A61M 60/148* (2021.01); *A61M 60/17* (2021.01); *A61M 60/237* (2021.01); *A61M 60/405* (2021.01); *A61M 60/419* (2021.01); *A61M 60/422* (2021.01);
(Continued)

(58) Field of Classification Search
CPC .. A61M 60/40; A61M 60/405; A61M 60/148; A61M 60/135; A61M 60/422; A61M 60/857; A61M 60/205; A61M 60/833; A61M 60/414; A61M 1/101; A61M 1/1015; A61M 1/1008; A61M 1/1031; A61M 1/1032; A61M 1/1036;
(Continued)

(56) References Cited

U.S. PATENT DOCUMENTS

| 3,608,088 A | 9/1971 | Dorman et al. |
| 4,135,253 A | 1/1979 | Reich et al. |

(Continued)

FOREIGN PATENT DOCUMENTS

| CN | 2412579 Y | 1/2001 |
| DE | 3616857 | 12/1987 |

(Continued)

OTHER PUBLICATIONS

Authorized Officer Malte Kaden, International Search Report for Application No. PCT/IB2008/000421, dated Nov. 7, 2008, 3 pages.
(Continued)

*Primary Examiner* — Tammie K Marlen
(74) *Attorney, Agent, or Firm* — Barnes & Thornburg LLP

(57) ABSTRACT

A device to assist the performance of a heart with at least one pump that is formed as a rotary pump and magnetically driven.

28 Claims, 3 Drawing Sheets

Related U.S. Application Data

No. 18/740,119, filed on Jun. 11, 2024, now Pat. No. 12,117,007, which is a continuation of application No. 18/363,166, filed on Aug. 1, 2023, now Pat. No. 12,104,600, which is a continuation of application No. 18/308,958, filed on Apr. 28, 2023, now Pat. No. 11,754,077, which is a continuation of application No. 18/087,083, filed on Dec. 22, 2022, now Pat. No. 11,674,517, which is a continuation of application No. 17/446,046, filed on Aug. 26, 2021, now Pat. No. 11,572,879, which is a continuation of application No. 16/282,948, filed on Feb. 22, 2019, now Pat. No. 11,123,540, which is a continuation of application No. 14/454,965, filed on Aug. 8, 2014, now Pat. No. 10,251,984, which is a continuation of application No. 13/555,318, filed on Jul. 23, 2012, now Pat. No. 8,801,590, which is a division of application No. 12/449,632, filed as application No. PCT/IB2008/000421 on Feb. 27, 2008, now Pat. No. 8,255,050.

(51) Int. Cl.
| | |
|---|---|
| *A61M 60/148* | (2021.01) |
| *A61M 60/17* | (2021.01) |
| *A61M 60/237* | (2021.01) |
| *A61M 60/405* | (2021.01) |
| *A61M 60/419* | (2021.01) |
| *A61M 60/422* | (2021.01) |
| *A61M 60/861* | (2021.01) |
| *F04D 13/02* | (2006.01) |
| *A61M 60/414* | (2021.01) |
| *A61M 60/833* | (2021.01) |

(52) U.S. Cl.
CPC ........ *A61M 60/523* (2021.01); *A61M 60/861* (2021.01); *A61M 60/414* (2021.01); *A61M 60/833* (2021.01)

(58) Field of Classification Search
CPC .... A61M 1/1029; A61M 1/122; A61M 1/125; F04D 13/027
See application file for complete search history.

(56) References Cited

U.S. PATENT DOCUMENTS

| | | | |
|---|---|---|---|
| 4,674,518 A | 6/1987 | Salo | |
| 4,895,557 A | 1/1990 | Moise et al. | |
| 5,308,319 A | 5/1994 | Ide et al. | |
| 5,324,177 A | 6/1994 | Golding et al. | |
| 5,449,342 A | 9/1995 | Hirose et al. | |
| 5,470,208 A | 11/1995 | Kletschka | |
| 5,503,615 A | 4/1996 | Goldstein | |
| 5,601,418 A | 2/1997 | Ohara et al. | |
| 5,676,526 A | 10/1997 | Kuwana et al. | |
| 5,695,471 A | 12/1997 | Wampler | |
| 5,840,070 A | 11/1998 | Wampler | |
| 5,921,913 A | 7/1999 | Siess | |
| 5,928,131 A | 7/1999 | Prem | |
| 5,947,703 A | 9/1999 | Nojiri et al. | |
| 5,964,694 A | 10/1999 | Sicss et al. | |
| 6,007,478 A | 12/1999 | Siess et al. | |
| 6,050,975 A | 4/2000 | Poirier | |
| 6,053,705 A | 4/2000 | Schob et al. | |
| 6,083,260 A | 7/2000 | Aboul-Hosn | |
| 6,100,618 A | 8/2000 | Schoeb et al. | |
| 6,152,704 A | 11/2000 | Aboul-Hosn et al. | |
| 6,155,969 A * | 12/2000 | Schima ................ A61M 60/113 600/16 |
| 6,176,848 B1 | 1/2001 | Rau et al. | |
| 6,351,048 B1 | 2/2002 | Schob et al. | |
| 6,506,146 B1 | 1/2003 | Mohl | |
| 6,508,787 B2 | 1/2003 | Erbel et al. | |
| 6,540,658 B1 | 4/2003 | Faschiano | |
| 6,589,030 B2 | 7/2003 | Ozaki | |
| 6,623,475 B1 | 9/2003 | Siess | |
| 6,884,210 B2 | 4/2005 | Nose et al. | |
| 6,949,066 B2 | 9/2005 | Bearnson et al. | |
| 7,699,586 B2 | 4/2010 | LaRose et al. | |
| 8,255,050 B2 | 8/2012 | Mohl | |
| 8,512,012 B2 | 8/2013 | Akdis et al. | |
| 9,616,157 B2 | 4/2017 | Akdis | |
| 11,351,356 B2 | 6/2022 | Mohl | |
| 2001/0039369 A1 | 11/2001 | Terentiev | |
| 2002/0102169 A1 | 8/2002 | Wampler | |
| 2003/0124007 A1 | 7/2003 | Schima et al. | |
| 2004/0236420 A1 | 11/2004 | Yamane et al. | |
| 2006/0089521 A1 | 4/2006 | Chang | |
| 2008/0214888 A1 | 9/2008 | Ben Shalom | |
| 2011/0238172 A1 | 9/2011 | Akdis | |

FOREIGN PATENT DOCUMENTS

| | | |
|---|---|---|
| DE | 19613564 C1 | 1/1998 |
| EP | 0075606 | 4/1983 |
| EP | 0371985 B1 | 6/1990 |
| EP | 0503839 | 9/1992 |
| EP | 1011753 | 6/2000 |
| EP | 1034808 | 9/2000 |
| EP | 0834326 B1 | 11/2004 |
| EP | 1727987 | 12/2006 |
| FR | 1187249 | 8/1959 |
| GB | 2347085 | 8/2000 |
| JP | 2005348996 | 12/2005 |
| WO | WO 1993/20860 | 10/1993 |
| WO | WO 1997/37698 | 10/1997 |
| WO | WO 1999/15213 | 4/1999 |
| WO | WO 2000/44417 | 8/2000 |
| WO | WO 2001/70300 | 9/2001 |
| WO | 2004/098677 A1 | 11/2004 |

OTHER PUBLICATIONS

Merkel et al., "Magnetic Bearing in INCOR Axial Blood Pump Acts as Multifunctional Sensor," Ninth International Symposium on Magnetic Bearings, 2004, 3 pages.

Mohl et al., "Intermittent Pressure Elevation of the Coronary Venous System as a Method to Protect Ischemic Myocardium," Interactive Cardio Vascular and Thoracic Surgery, vol. 4, 2005, pp. 66-69.

Ramsden et al., "A Rotary Blood Pump," University of Technology, Sydney, Mar. 2007, 4 pages.

Syeda et al., "The Salvage Potential of Coronary Sinus Interventions: Meta-Analysis and Pathophysiologic Consequences," The Journal of Thoracic and Cardiovascular Surgery, vol. 127, No. 6 (Jun. 2004), pp. 1703-1712.

Petition for Inter Partes Review of U.S. Pat. No. 11,351,356, Filed: Nov. 5, 2024.

Akamatsu et al., "Development of Terumo implantable left ventricular assist system (T-ILVAS) with a magnetically suspended centrifugal pump", J Artif Organs 1999, vol. 2, pp. 3-7.

Plaintiff's Supplemental Initial Response to Defendants' Supplemental Initial Invalidity and Unenforceability Contentions, Case No. 1:23-cv-16257, Sep. 20, 2024.

Rose et al., "Long-Term Use of a Left Ventricular Assist Device for End-Stage Heart Failure", The New England Journal of Medicine Nov. 15, 2001, vol. 345, No. 20, pp. 1435-1443.

HeartMate® II LVAS: Patient Management Guidelines, Dec. 14, 2006.

Schulman et al., "Comparisons of infection complications between continuous flow and pulsatile flow left ventricular assist devices", The Journal of Thoracic and Cardiovascular Surgery 2007, vol. 133, No. 3, pp. 841-842.

Larose et al., Heartware—A Novel Miniaturized Passive Maglev Centrifugal VAD, ASAIO Journal Mar. 2004, vol. 50, No. 2, p. 137.

Akamatsu et al., "Chronic Animal Experiment with Magnetically Suspended Centrifugal Pump", Artificial Organs 1997, vol. 21, No. 7, pp. 635-638.

(56) References Cited

OTHER PUBLICATIONS

Bottone et al., "Magnetos for automobilists, how made and how used", Crosby Lockwood and Son, Ch. 1 (1907) (accessed at https://archive.org/details/magnetosforauto00bottgoog/page/n6/mode/2up).

"Ignition magneto", accessed via https://en.wikipedia.org/wiki/Ignition_magneto (last accessed Oct. 28, 2024).

Miracor's Response to Exhibit A-1 (Bourque-2001) of Supplemental Invalidity Contentions, dated Sep. 20, 2024.

Allaire et al., "Prototype Continuous Flow Ventricular Assist Device", J. Artificial Organs 1996, vol. 20, No. 7, pp. 582-590.

Kung and Hart, "Design Considerations for Bearingless Rotary Pumps", J. Artificial Organs 1997, vol. 21, No. 7, pp. 645-650.

Declaration of Sylvia D. Hall-Ellis, dated Nov. 4, 2024.

U.S. Pat. No. 11,351,356 File History.

Barletta et al., "Design of a Bearingless Blood Pump", Third International Symposium on Magnetic Suspension Technology, pp. 265-274, vol. 1, Jul. 1, 1996.

Bearnson et al., "HeartQuest Ventricular Assist Device Magnetically Levitated Centrifugal Blood Pump", pp. 339-346, published 2006.

Burgreen et al., "Computational Fluid Dynamics Analysis of a Maglev Centrifugal Left Ventricular Assist Device", pp. 874-880, published 2004.

Frazier et al., "Total Heart Replacement with Dual Centrifugal Ventricular Assist Devices", pp. 224-229, ASAIO Journal 2005.

Masuzawa et al., "Magnetically Suspended Centrifugal Blood Pump with an Axially Levitated Motor", pp. 631-638, 2003 International Society for Artificial Organs.

Schob, "Centrifugal pump without bearings or seals", pp. 34-37, World Pumps Jul. 2002.

Qian et al., "Permanent magnetic-levitation of rotating impeller: a decisive breakthrough in the centrifugal pump", pp. 36-38, Journal of Medical Engineering & Technology, vol. 26, No. 1 (Jan./Feb. 2002).

Bourque, et al., "HeartMate III: Pump Design for a Centrifugal LVAD with a Magnetically Levitated Rotor", ASAIO Journal 2001, pp. 401-405.

Bourque, et al., "In Vivo-Assessment of a rotary Left Ventricular Assist Device-induced Artificial Pulse in the Proximal and Distal Aorta", Artif Organs, vol. 30, No. 8, 2006, 6 pgs.

Petition for Inter Partes Review of U.S. Pat. No. 11,754,077, filed Nov. 27, 2024.

Petition for Inter Partes Review of U.S. Pat. No. 11,674,517, filed Nov. 26, 2024.

Petition for Inter Partes Review of U.S. Pat. No. 11,351,357, filed Nov. 26, 2024.

Petition for Inter Partes Review of U.S. Pat. No. 11,376,415, filed Nov. 26, 2024.

Petition for Inter Partes Review of U.S. Pat. No. 11,572,879, filed Nov. 27, 2024.

Exhibit 9 of Complaint, dated Nov. 27, 2023, Case No. 1:23-cv-16257 (IPR2025-00112).

Miracor's Response to Exhibit B-1 (Bourque-2001) of Supplemental Invalidity Contentions, dated Apr. 26, 2024, Case No. 1:23-cv-16257 (IPR2025-00112).

Exhibit 10 of Complaint, dated Nov. 27, 2023, Case No. 1:23-cv-16257 (IPR2025-00113).

Miracor's Response to Exhibit A-1 (C-1) (Bourque-2001) of Supplemental Invalidity contentions, dated Sep. 20, 2024, Case No. 1:23-cv-16257 (IPR2025-00113).

Exhibit 11 of Complaint, dated Nov. 27, 2023, Case No. 1:23-cv-16257 (IPR-2025-00114).

Miracor's Response to Exhibit D-1 (Bourque-2001) of Supplemental Invalidity Contentions, Case No. 1:23-cv-16257 (IPR2025-00114).

Exhibit 12 of Complaint, dated Nov. 27, 2023, Case No. 1:23-cv-16257 (IPR2025-00115).

Miracor's Response to Exhibit A-1 (E-1) (Bourque-2001) of Supplemental Invalidity Contentions, dated Sep. 20, 2024, Case No. 1:23-cv-16257 (IPR2025-00115).

Miracor's Supplemental Initial Response to Invalidity Contentions, dated Sep. 20, 2024, Case No. 1:23-cv-16257 (IPR2025-00116).

Exhibit 13 of Complaint, dated Nov. 27, 2023, Case No. 1:23-cv-16257 (IPR2025-00116).

Miracor's Response to Exhibit F-1 (Bourque-2001) of Supplemental Invalidity Contentions, dated Sep. 20, 2024, Case No. 1:23-cv-16257 (IPR2025-00116).

Declaration of Peter Crosby for U.S. Pat. No. 11,351,357, dated Nov. 22, 2024, IPR2025-00112.

Miracor's Supplemental Initial Response to Invalidity Contentions dated Sep. 20, 2024, Case No. 1:23-cv-16257 (IPR2025-00112).

Declaration of Peter Crosby for U.S. Pat. No. 11,376,415, dated Nov. 22, 2024, IPR2025-00113.

Miracor's Supplemental Initial Response to Invalidity Contentions, dated Sep. 20, 2024, Case No. 1:23-cv-16257 (IPR2025-00113).

Declaration of Peter Crosby for U.S. Pat. No, 11,572,879, dated Nov. 22, 2024, IPR2025-00114.

Miracor's Supplemental Initial Response to Invalidity Contentions, dated Sep. 20, 2024, Case No. 1:23-cv-16257 (IPR2025-00114).

Declaration of Peter Crosby for U.S. Pat. No. 11,674,517, dated Nov. 22, 2024, IPR2025-00115.

Miracor's Supplemental Initial Response to Invalidity Contentions, dated Sep. 20, 2024, Case No. 1:23-cv-16257 (IPR2025-00115).

Declaration of Peter Crosby for U.S. Pat. No. 11,754,077, dated Nov. 22, 2024, IPR2025-00116.

Declaration of Peter Crosby for U.S. Pat. No. 11,351,356, dated Nov. 5, 2024, IPR2025-00096.

* cited by examiner

DEVICE TO ASSIST THE PERFORMANCE OF A HEART

CROSS-REFERENCE TO RELATED APPLICATIONS

This application is a continuation of U.S. application Ser. No. 18/795,656 filed on Aug. 6, 2024 which is a continuation of U.S. application Ser. No. 18/740,119 filed on Jun. 11, 2024, (now U.S. Pat. No. 12,117,007, issued Oct. 15, 2024), which is a continuation of U.S. application Ser. No. 18/363,166 filed on Aug. 1, 2023 (now U.S. Pat. No. 12,104,600, issued Oct. 1, 2024) and is continuation of and claims the benefit of priority to U.S. application Ser. No. 18/308,958 filed on Apr. 28, 2023 (now U.S. Pat. No. 11,754,077, issued Sep. 12, 2023), which is a continuation of and claims priority to U.S. application Ser. No. 18/087,083 filed on Dec. 22, 2022 (now U.S. Pat. No. 11,674,517, issued Jun. 13, 2023), which is a continuation of and claims priority to U.S. application Ser. No. 17/446,046 filed on Aug. 26, 2021 (now U.S. Pat. No. 11,572,879, issued Feb. 7, 2023), which is a continuation of U.S. application Ser. No. 16/282,948 filed on Feb. 22, 2019 (now U.S. Pat. No. 11,123,540, issued Sep. 21, 2021), which is a continuation of U.S. application Ser. No. 14/454,965 filed on Aug. 8, 2014 (now U.S. Pat. No. 10,251,984, issued Apr. 9, 2019), which is a continuation of U.S. application Ser. No. 13/555,318 filed on Jul. 23, 2012 (now U.S. Pat. No. 8,801,590, issued Aug. 12, 2014), which is a divisional of U.S. application Ser. No. 12/449,632 filed on Aug. 18, 2009 (now U.S. Pat. No. 8,255,050, issued Aug. 28,2012), which is the U.S. national phase of International Application PCT/IB2008/000421filed on Feb. 27, 2008, which designated the U.S. and claims benefit of AT A306/2007filed Feb. 27, 2007, the entire contents of each of these prior applications are hereby incorporated by reference.

BACKGROUND

After a heart failure, for example a cardiac infarction or other reasons for the decrease in the performance of a heart, it is of essential importance for intensive care medicine to normalise and stabilise the cardiac function again as rapidly as possible. When for example the volume output of the heart is distinctly reduced as a result of a failure, it is particularly important to reliably and rapidly re-establish a corresponding peripheral blood flow in order to prevent secondary damage. The use of heart-lung machines basically allows the essential vital functions to be maintained. A specific adaptation to the respective actual requirements generally does not take place with such devices, however. Rather, conventional heart-lung machines are devices which, using external pumps, maintain a forced circulation of blood without systematically entering into the respective requirements of the heart which has been weakened or subjected to a failure.

In surgical interventions, particularly in the vein area, it has already been proposed to carry out retroinfusion, controlled by venous pressure, from or in veins of the body with the suction" of fluid and return of the fluid via a pump. Conventional catheters are used here, the lumina of which allow a suction of fluid and via the lumina of which the return is made possible at a suitable site. Known devices, particularly for the retroinfusion of blood in coronary veins in the area of myocardial protection during a brief coronary artery closure within a cardiological intervention, are generally devised so that a balloon dilatation of an arterioscle-rotically constricted coronary artery is carried out. In these cases, a compensation which is adapted to the intervention briefly taking place respectively can be carried out by the return of blood which has been drawn off in veins. For a continuous restitution of the full function of a heart, however, the criteria are not taken into account which would be relevant for the full function of the heart, and an intensive provision over a particular period of time is therefore not provided with such devices. At the same time, the provision of the other organs must also be maintained.

In the device known from AT 407 960 B for assisting the performance of a heart, fluid is removed from blood vessels via an external pump and is returned into blood vessels via a return catheter, in which the returned quantity of fluid is regulated as a function of measurement values, with a heart ventricle catheter being provided to obtain these measurement values. The known device comprised a heart ventricle catheter which is equipped in the cardiac chamber with sensors to measure the volume of fluid per unit of time, in which these sensors, in the introduced state of the heart ventricle catheter, lie in the cardiac chamber and these sensors are connected with an evaluation circuit in which the ratio of the diastolic volume to the systolic volume is evaluated per heartbeat or per unit of time in particular the discharge rate and/or the deviation of the volume conveyed per unit of time by the heart from a defined rated value is evaluated, for example the rated value, calculated from physically specific data for the cardiac output. The signal which is generated in this way is passed to the pump, via which fluid is withdrawn from the cardiac chamber and is recirculated as a function of the generated signal.

SUMMARY

A fluid flow which is improved by the pump is to be developed in a way in which the mechanical stress of highly sensitive fluids, such as blood for example, can be kept as low as possible and nevertheless the corresponding improvement to circulation can be ensured at desired locations. A completely impervious separation of the rotor from the drive wheel is achieved by a magneto coupling which is provided according to the invention, which eliminates axial passages between the drive wheel and the rotor lying distally on the outside.

The rotor itself can follow design principles such as described for example in WO 01/70300 A1. The rotary pump shown and described there for conveying blood and other highly sensitive fluids is formed as an external electromagnetically driven pump which is not directly suitable for incorporation into a catheter. However, for the desired conveying capacity with the axial pump according to the invention, provision is also made according to the invention that the rotor has guide surfaces to produce centrifugal flow components.

The driving fluid can be used within the scope of the invention in order to be able to operate a balloon for retroperfusion. The embodiment is preferably devised hereby so that the lumina for the driving fluid are guided through an expandable balloon surrounding the catheter in a sealing manner, and that the lumina have separately controllable closure members via which driving fluid can arrive in the balloon or out of the balloon into the respective lumina, in which preferably the closure members are formed as magneto valves. On inflation of the balloon, additional driving medium is required which can be discharged again on collapsing of the balloon. This is possible extracorporeally on the drive side by means of a reservoir.

The embodiment to assist the performance of a heart according to the invention, in which fluid is conveyed in blood vessels with the use of a pump and the conveyed quantity is able to be regulated as a function of measurement values of a heart ventricle catheter, from which the cardiac output is determined, proceeds from a development according to 407 960 B and is characterised substantially in that the pump is formed as an intravasal rotary pump at the periphery or at the distal end of the catheter, the rotor of which, lying on the outside, is connected via a magneto coupling with the drive which is arranged inside the catheter.

BRIEF DESCRIPTION OF DRAWINGS

The invention is explained in further detail below by use of an exemplary embodiment which is illustrated diagrammatically in the drawings, in which.

DETAILED DESCRIPTION

Figure 1:
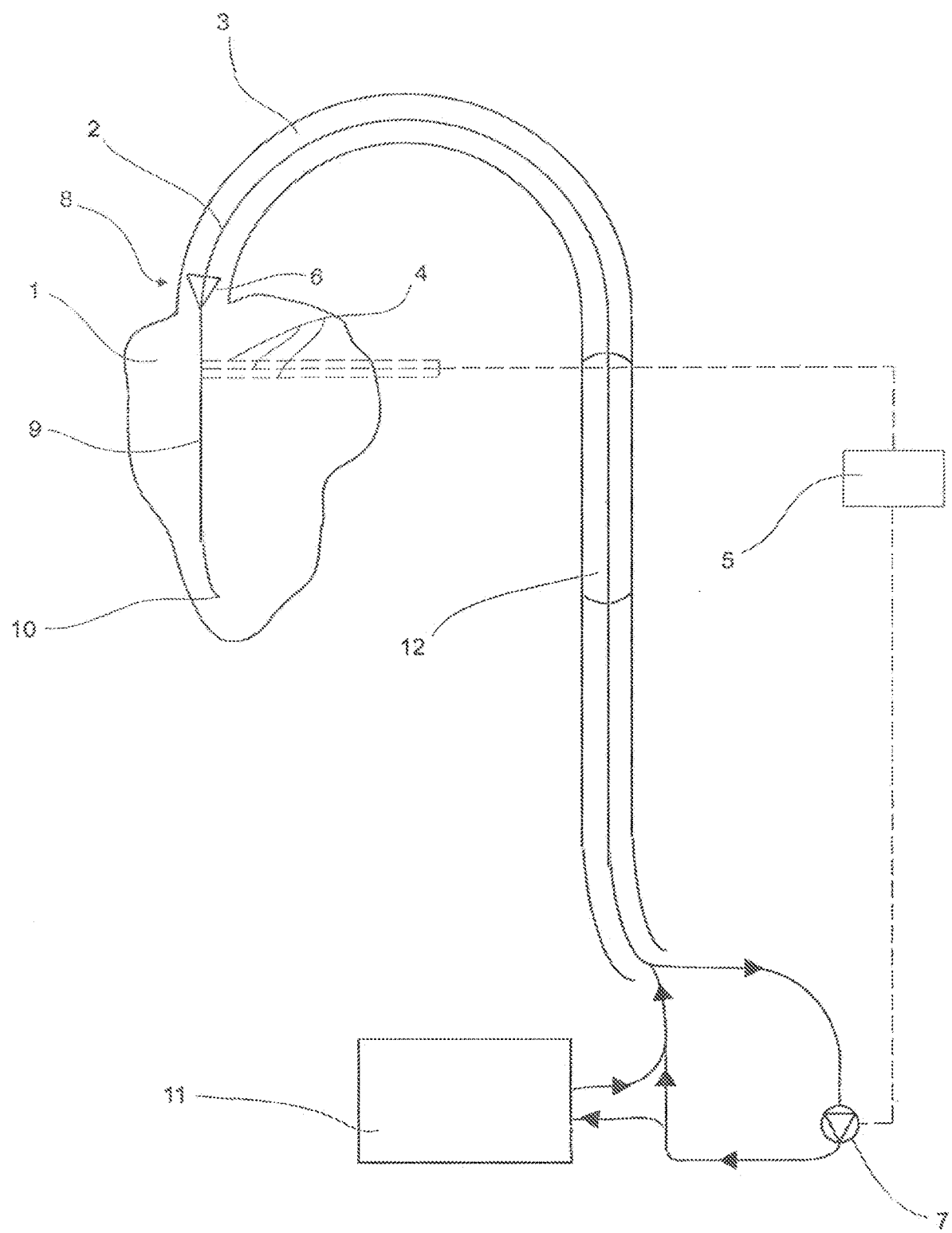
FIG. 1 shows a diagrammatic illustration of the arrangement of the pump and of the drive.

In FIG. 1, a heart is designated by 1, into which a heart ventricle catheter 2 is introduced. The catheter is introduced here for example via the femoral artery and the aortic arch 3 into the heart chamber and carries a series of sensors 4 via which the volume can be determined. The measurement signals are passed to a control arrangement 5. The heart ventricle catheter is formed with several lumina, as additionally illustrated below in further figures of the drawings, with fluid being supplied via such lumina to drive a rotor, arranged at the distal end, which forms the pump to assist the blood circulation and is designated by 6 in FIG. 1. The positioning of this rotor is indicated in FIG. 1 by the arrow 8. The driving medium for the rotor or the pump is guided in a circular flow by means of a fluid pump 7 which can be regulated in a synchronised manner as a function of the control signals generated in the control arrangement 5. The distal region in which the pump is arranged is designated diagrammatically by 8, the catheter 2 having at its distal end a tube 9 leading to the suction end 10. A reservoir for driving fluid is designated by 11, which provides additional driving medium for filling the balloon 12 serving for an occlusion of the artery, and which receives again the volume of driving medium occurring on deflation of the balloon.

The volumetric measurement in the cardiac chamber allows differences to be reliably detected between the diastolic and systolic volume and allows corresponding correction signals to be made available for the output of the synchronised fluid pump 7. Furthermore, in the control circuit 5, corresponding fixed values can be provided, such as for example a defined cardiac output, which is referred to on deviation of the measured cardiac output to control the pump.

A retroperfusion can take place via a conventional balloon catheter which is occluded in a correspondingly synchronized manner, so that the directed return is in fact guaranteed during the diastole. Hereby the corresponding measurement values for the heart rate or for the correct moment of the diastole can be obtained from ECG data.

Figure 2:
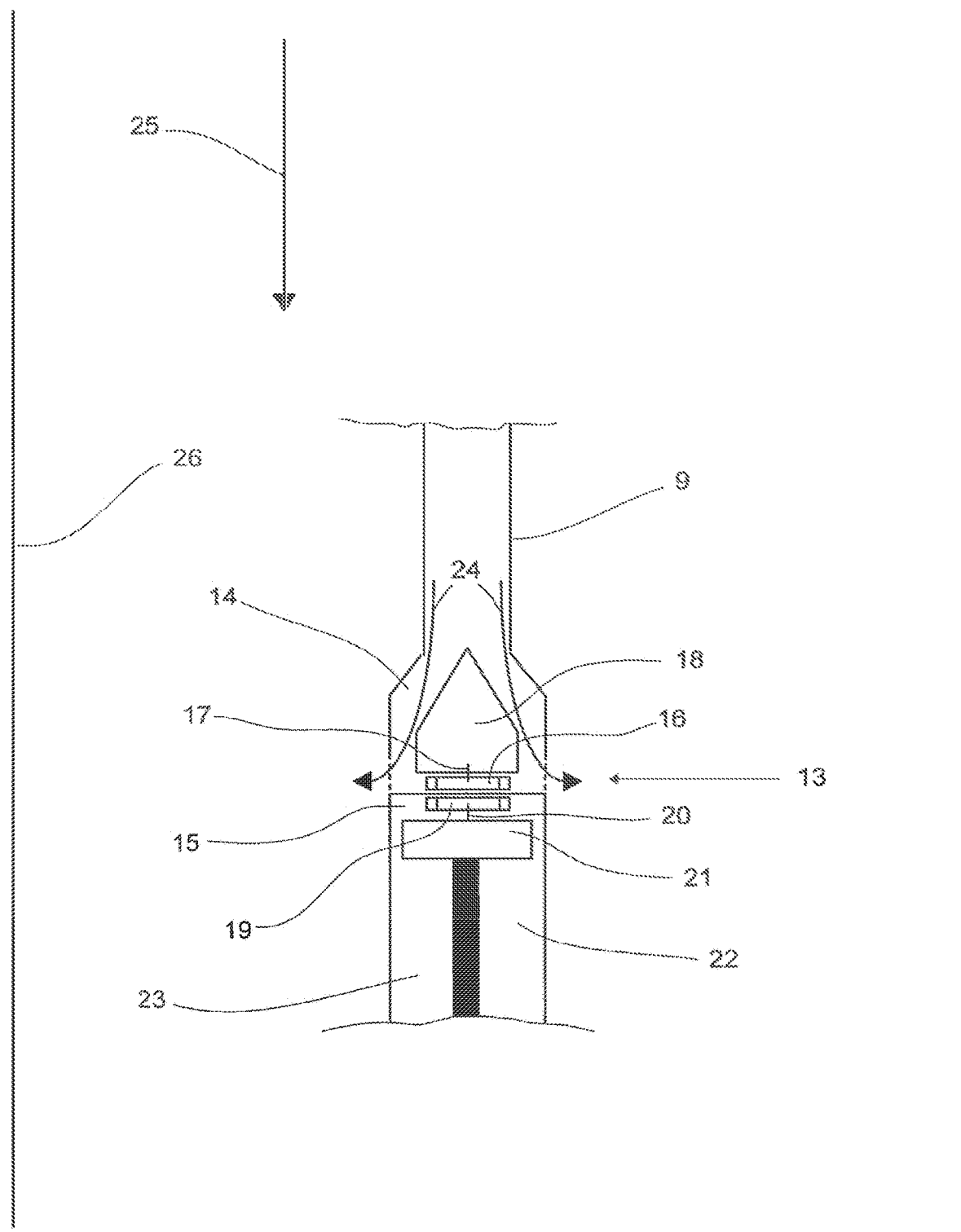
FIG. 2 shows a diagrammatic illustration of the distal end of a catheter which is used according to the invention.

In FIG. 2, the distal end of a modified catheter 2 is now illustrated. The end side 13 of this catheter has two pocket-shaped chambers 14 and 15, in which bar magnets are respectively arranged. The bar magnet 16 is connected here at the distal end outwards via a shaft 17 with a rotor 18, whereas the bar magnet 19 lying on the inside is connected via a shaft 20 with a drive wheel 21. The drive wheel 21 is formed here as a paddle wheel and is acted upon with fluid via a lumen 22, this fluid flowing off again via the lumen 23 of the catheter. The rotation of the paddle wheel 21 is regulated here accordingly by corresponding control of the fluid pressure in the lumen 22 serving for the supply of fluid, in which the magnet 19, which is connected so as to be locked against relative rotation with the paddle wheel 21, is set into corresponding rotation. At the outer side, which is completely sealed with respect to the lumina 22 and 23, the magnet 16 is subsequently entrained accordingly and drives the rotor 18 via the shaft 17, whereby a flow is formed in the region of the tube 9, as is indicated by the arrows 24, and which assists the natural blood flow in the vessel 26, illustrated by the arrow 25.

Figure 3:
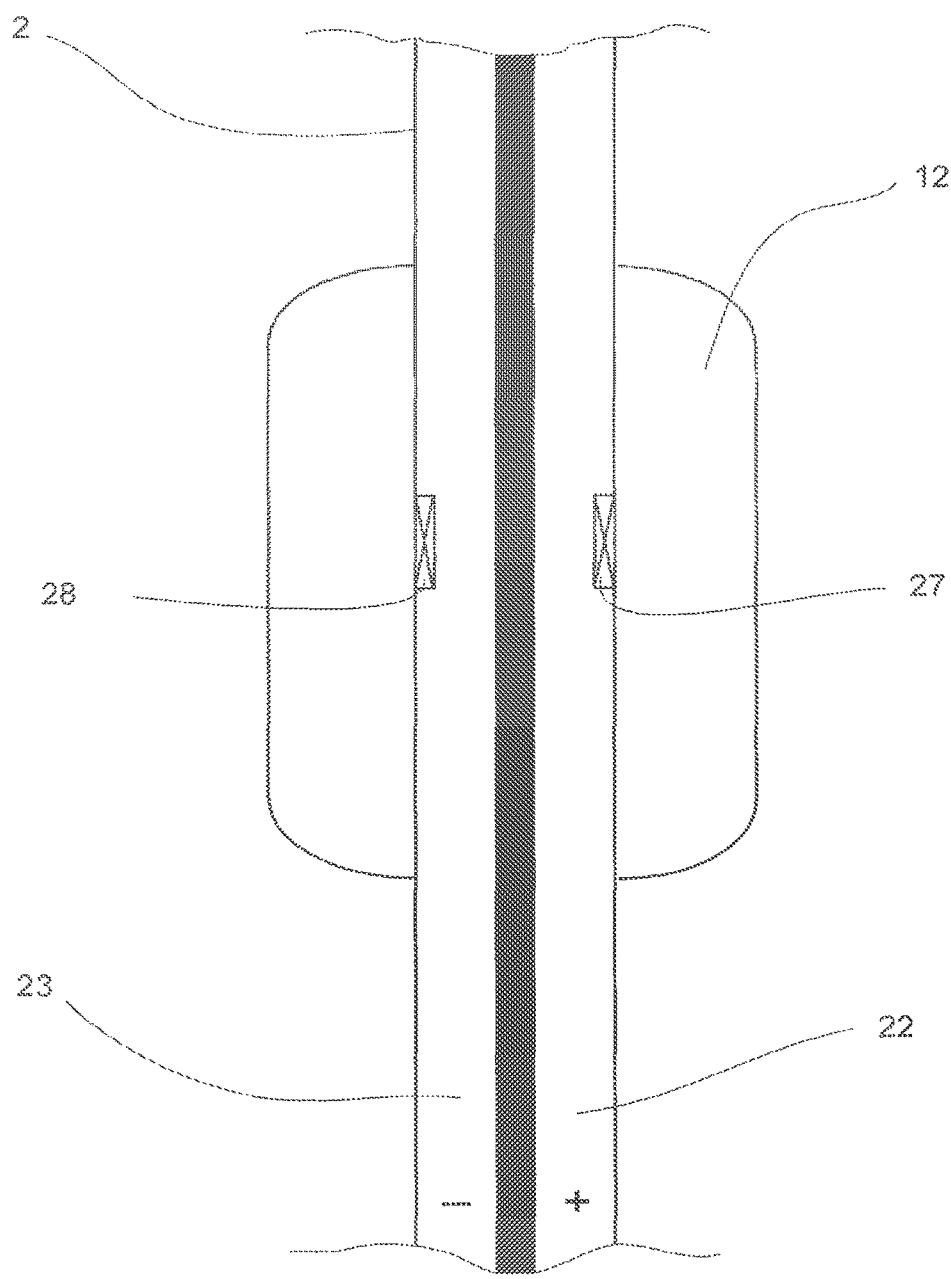
FIG. 3 shows an enlarged illustration of the part of the catheter bearing the balloon, in section.

In FIG. 3, the partial region of the balloon 12, which is connected in a sealing manner to the catheter 2, is illustrated on an enlarged scale. The two lumina leading away from the fluid pump 7 and back to the fluid pump 7 are designated in turn by 22 and 23. In the region of the balloon 12, the wall of these lumina is provided with valves which can be actuated magnetically for example. The valves are indicated diagrammatically by 27 and An opening of the valve 27 leads to the fluid, coming from the fluid pump 7, which is under pressure, which is indicated by the "+" sign, being pumped into the balloon 12, with which the overall quantity of the circulating driving fluid would of course be reduced, in so far as the reservoir 11, indicated diagrammatically in FIG. 1, is not provided. By closing the valve 27, the occlusion is closed off, the collapsing of the balloon 12 being able to be brought about by opening the valve 28 and the fluid now being drawn off via the lumen 23, leading back to the pump, which lumen 23 is at a slightly lower pressure which is indicated by the "−" sign. As the overall volume of the fluid in the circulating system is now to be reduced, a portion of this volume must be pumped back again into the reservoir 11 according to FIG. 1.

What is claimed is:
1. A heart assist pump device configured to be positioned within a patient's body and comprising:
   a blood flow path comprising:
      an inflow tube with a distal suction end configured to be inserted into a ventricle of a heart, wherein the inflow tube is substantially linear and comprises a central axis, wherein the distal suction end is aligned with the central axis;
      a first chamber comprising one or more side walls and a substantially planar bottom wall having an inner surface that is located at a position that is axially opposite of the distal suction end, the first chamber in fluid communication with the inflow tube, wherein the first chamber is axially aligned with the distal suction end and with the central axis; and
      a blood outflow path located downstream of the inflow tube and in fluid communication with the first chamber and with a blood vessel of the body, and configured to direct blood in at least one direction that is not axially aligned with the central axis;
   a magnetic rotor assembly comprising a rotor and a first magnetic device, wherein the entire magnetic rotor assembly is located within the first chamber, wherein the first magnetic device is a single magnetic device that is axially adjacent to the rotor and rigidly coupled to the rotor;

a second magnetic device associated with, and sealed from, the magnetic rotor assembly and wherein the second magnetic device is configured to couple magnetically with the first magnetic device to rotate the magnetic rotor assembly, wherein the second magnetic device is a single magnetic device, wherein the magnetic rotor assembly and the second magnetic device are axially aligned with the central axis and with the distal suction end of the inflow tube, and wherein a magnetic coupling between the first magnetic device and the second magnetic device is configured to rotate the magnetic rotor assembly, and to orient the magnetic rotor assembly within the first chamber to control an axial position of the magnetic rotor assembly within the first chamber such that the magnetic rotor assembly is entirely spaced away from the one or more side walls of the first chamber by the magnetic coupling to define a gap between the one or more side walls of the first chamber and the magnetic rotor assembly, the gap configured for blood flow therethrough, wherein the magnetic rotor assembly further comprises guide surfaces in fluid communication with the blood flowing through the blood flow path and the blood outflow path, the guide surfaces configured to produce centrifugal components within the blood within the first chamber during rotation of the magnetic rotor assembly, wherein at least the guide surfaces of the magnetic rotor assembly are configured to drive the blood flow along the blood outflow path.

2. The heart assist pump device of claim 1, further comprising a second chamber that surrounds the second magnetic device and comprises one or more walls that seal the second magnetic device from the magnetic rotor assembly.

3. The heart assist pump device of claim 1, wherein the guide surfaces are spaced axially away from the inner surface of the substantially planar bottom wall.

4. The heart assist pump device of claim 3, wherein the second magnetic device radially overlaps at least part of the first magnetic device and wherein the second magnetic device is axially closer to the first magnetic device than to the guide surfaces of the rotor.

5. The heart assist pump device of claim 1, wherein at least part of the blood outflow path is configured to direct the blood driven by the guide surfaces in a direction that is substantially perpendicular to the central axis.

6. The heart assist pump device of claim 1, wherein the guide surfaces are configured to drive the blood within the first chamber into the blood outflow path in a direction that is substantially perpendicular to the inflow tube and to the central axis.

7. The heart assist pump device of claim 1, wherein the second magnetic device is spaced axially from the guide surfaces of the rotor.

8. The heart assist pump device of claim 1, wherein the blood vessel is an artery.

9. The heart assist pump device of claim 1, wherein the blood vessel is an aorta.

10. The heart assist pump device of claim 1, wherein the ventricle is a left ventricle.

11. The heart assist pump device of claim 1, further comprising a control arrangement comprising at least one sensor configured to generate a control signal, and a controller configured to receive the generated control signal.

12. The heart assist pump device of claim 11, wherein the control arrangement is configured to control the heart assist pump device.

13. The heart assist pump device of claim 1, wherein the magnetic coupling is configured to control a radial position of the magnetic rotor assembly within the first chamber such that the magnetic rotor assembly is entirely spaced apart from the one or more side walls of the first chamber.

14. A method for assisting the blood circulation of a heart in a body, comprising:
  providing a heart assist device configured to be positioned within the body, comprising:
    a blood flow path comprising:
      an inflow tube with a distal suction end configured to be inserted into a left ventricle of a heart, wherein the inflow tube is substantially linear and comprises a central axis, wherein the distal suction end is aligned with the central axis;
      a first chamber comprising one or more side walls and a substantially planar bottom wall having an inner surface that is located at a position that is axially opposite of the distal suction end, wherein the first chamber is in fluid communication with the inflow tube, and wherein the first chamber is axially aligned with the distal suction end and with the central axis; and
      a blood outflow path located downstream of the inflow tube and in fluid communication with the first chamber and with an aorta of the body, and configured to direct blood in at least one direction that is not axially aligned with the central axis;
    a magnetic rotor assembly comprising a rotor and a first magnetic device wherein the entire magnetic rotor assembly is located within the first chamber, and wherein the first magnetic device is a single magnetic device that is axially adjacent to the rotor and rigidly coupled to the rotor;
    a second magnetic device associated with, and sealed from, the magnetic rotor assembly and wherein the second magnetic device is configured to magnetically couple with the first magnetic device to rotate the magnetic rotor assembly, wherein the second magnetic device is a single magnetic device,
    wherein a magnetic coupling between the first magnetic device and the second magnetic device is further configured to orient and control an axial position of the magnetic rotor assembly within the first chamber relative to the one or more side walls of the first chamber,
    wherein the magnetic rotor assembly and the second magnetic device are axially aligned with the distal suction end of the inflow tube and with the central axis;
    a gap between the one or more side walls of the first chamber and the magnetic rotor assembly, the gap configured for blood flow therethrough,
    wherein the magnetic rotor assembly comprises guide surfaces in fluid communication with the blood flowing through the blood flow path and the outflow blood path, the guide surfaces configured to produce centrifugal components within the blood within the first chamber during rotation of the magnetic rotor assembly,
    wherein at least the guide surfaces of the magnetic rotor assembly are configured to drive the blood flow along the blood outflow path;

orienting an axial position of the magnetic rotor assembly within the first chamber via the magnetic coupling such that the magnetic rotor assembly remains entirely spaced away from the walls of the first chamber and such that the gap between the one or more side walls of the first chamber and the magnetic rotor assembly is defined;

positioning the heart assist pump device within the body;

inserting the suction end of the inflow tube into the left ventricle;

activating the heart assist pump device;

rotating the magnetic rotor assembly via the magnetic coupling;

maintaining the orienting of an axial position of the magnetic rotor assembly within the first chamber during the rotation of the magnetic rotor assembly;

suctioning the blood from the ventricle and into the inflow tube;

driving the blood through the blood outflow path; and conveying the blood through the blood outflow path to the aorta.

15. The method of claim 14, wherein the heart assist pump device further comprises a second chamber that surrounds the second magnetic device and comprises one or more walls that seal the second magnetic device from the magnetic rotor assembly.

16. The method of claim 14, wherein the guide surfaces are spaced axially away from the inner surface of the substantially planar bottom wall.

17. The method of claim 16, wherein the second magnetic device radially overlaps at least part of the first magnetic device and wherein the second magnetic device is axially closer to the first magnetic device than to the guide surfaces of the rotor.

18. The method of claim 14, further comprising configuring at least part of the blood outflow path to direct the blood driven by the guide surfaces in a direction that is substantially perpendicular to the central axis.

19. The method of claim 14, comprising configuring the guide surfaces to drive the blood within the first chamber into the blood outflow path in a direction that is substantially perpendicular to the inflow tube and to the central axis.

20. The method of claim 14, wherein the heart assist pump device further comprises a control arrangement comprising at least one sensor configured to generate a control signal, and a controller configured to receive the generated control signal.

21. The method of claim 20, controlling the heart assist pump device with the control arrangement.

22. A method for assisting the blood circulation of a heart in a body, comprising:

providing a heart assist device comprising:

a blood flow path comprising:

an inflow tube with a distal suction end configured to be inserted into a left ventricle of a heart, wherein the inflow tube is substantially linear and comprises a central axis, wherein the distal suction end is aligned with the central axis;

a first chamber comprising one or more walls and a substantially planar bottom wall having an inner surface that is located at a position that is axially opposite of the distal suction end, wherein the first chamber is in fluid communication with the inflow tube, and wherein the first chamber is axially aligned with the central axis and with the distal suction end; and a blood outflow path located downstream of the inflow tube and in fluid communication with the first chamber and with an aorta of the body, and configured to direct blood in at least one direction that is not axially aligned with the central axis;

a magnetic rotor assembly comprising a rotor and a first magnetic device located within the first chamber, wherein the first magnetic device is a single magnetic device rigidly coupled to the rotor and wherein the entire magnetic rotor assembly is located within the first chamber, and wherein an axial position of the magnetic rotor assembly is oriented by the magnetic coupling to space the magnetic rotor assembly away from the one or more side walls of the first chamber;

a second magnetic device associated with, and sealed from, the magnetic rotor assembly and wherein the second magnetic device is configured to magnetically couple with the first magnetic device to rotate and orient the magnetic rotor assembly within the first chamber, wherein the second magnetic device is a single magnetic device, wherein the magnetic rotor assembly and the second magnetic device are axially aligned with the distal suction end and the central axis;

a gap between the one or more side walls of the first chamber and the magnetic rotor assembly, the gap configured for blood flow therethrough, the gap defined by the spacing of the magnetic rotor assembly from the one or more side walls of the first chamber, wherein the magnetic rotor assembly comprises guide surfaces in fluid communication with the blood flowing through the blood flow path and the outflow blood path, the guide surfaces configured to produce centrifugal components within the blood within the first chamber during rotation of the magnetic rotor assembly, wherein the guide surfaces are spaced axially away from the inner surface of the substantially planar bottom wall, wherein at least the guide surfaces of the magnetic rotor assembly are configured to drive the blood flow along the blood outflow path;

orienting an axial position of the magnetic rotor assembly via the magnetic coupling such that the magnetic rotor assembly remains entirely spaced away from the walls of the first chamber and such that the gap between the one or more side walls of the first chamber and the magnetic rotor assembly is defined;

positioning the heart assist pump device within the body;

inserting the suction end of the inflow tube into the left ventricle;

controlling an axial position of the magnetic rotor assembly within the first chamber;

activating the heart assist pump device;

rotating the magnetic rotor assembly via the magnetic coupling;

maintaining the orienting of the magnetic rotor assembly within the first chamber and maintaining the controlling of the axial position of the magnetic rotor assembly within the first chamber during the rotation of the magnetic rotor assembly;

suctioning the blood from the ventricle and into the inflow tube;

driving the blood through blood outflow path; and conveying the blood through the blood outflow path to the aorta.

23. The method of claim 22, wherein the heart assist pump device further comprises a second chamber that surrounds the second magnetic device and comprises one or more walls that seal the second magnetic device from the magnetic rotor assembly.

24. The method of claim 22, wherein the second magnetic device radially overlaps at least part of the first magnetic device and wherein the second magnetic device is axially closer to the first magnetic device than to the guide surfaces of the rotor.

25. The method of claim 22, further comprising configuring at least part of the blood outflow path to direct the blood driven by the guide surfaces in a direction that is substantially perpendicular to the central axis.

26. The method of claim 22, comprising configuring the guide surfaces to drive the blood within the first chamber into the blood outflow path in a direction that is substantially perpendicular to the inflow tube and to the central axis.

27. The method of claim 22, wherein the heart assist pump device further comprises a control arrangement comprising at least one sensor configured to generate a control signal, and a controller configured to receive the generated control signal.

28. The method of claim 27, controlling the heart assist pump device with the control arrangement.

* * * * *